US010772489B2

(12) United States Patent
Govari et al.

(10) Patent No.: US 10,772,489 B2
(45) Date of Patent: Sep. 15, 2020

(54) GUIDEWIRE NAVIGATION FOR SINUPLASTY

(71) Applicants: Acclarent, Inc., Menlo Park, CA (US); Biosense Webster (Israel) Ltd., Yokneam (IL)

(72) Inventors: Assaf Govari, Haifa (IL); Randy J. Kesten, Mountain View, CA (US); Andres C. Altmann, Haifa (IL); Thomas R. Jenkins, Alameda, CA (US); Vadim Gliner, Haifa (IL)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 825 days.

(21) Appl. No.: 14/792,823

(22) Filed: Jul. 7, 2015

(65) Prior Publication Data
US 2016/0007842 A1 Jan. 14, 2016

Related U.S. Application Data

(60) Provisional application No. 62/052,391, filed on Sep. 18, 2014, provisional application No. 62/022,607, filed on Jul. 9, 2014.

(51) Int. Cl.
*A61B 5/06* (2006.01)
*A61B 1/07* (2006.01)
(Continued)

(52) U.S. Cl.
CPC ............... *A61B 1/07* (2013.01); *A61B 1/233* (2013.01); *A61B 5/062* (2013.01); *A61B 17/24* (2013.01);
(Continued)

(58) Field of Classification Search
CPC .......... A61B 34/20; A61B 5/062; A61B 1/07; A61B 1/233; A61B 17/24; A61B 90/14;
(Continued)

(56) References Cited

U.S. PATENT DOCUMENTS 5,967,980 A 10/1999 Ferre
6,016,439 A 1/2000 Acker
(Continued)

FOREIGN PATENT DOCUMENTS

CN 103118583 5/2013
CN 103298514 9/2013
(Continued)

OTHER PUBLICATIONS

Bulu, H. et al., "Comparison of 3D Segmentation Algorithms for Medical Imaging." Twentieth IEEE International Symposium on Computer-Based Medical Systems, 2007 (CBMS '07) 6 pages.
(Continued)

*Primary Examiner* — Peter Luong
(74) *Attorney, Agent, or Firm* — Todd J. Burns (57) ABSTRACT

Apparatus, including a guidewire having a distal end, that is configured to be inserted into proximity with a nasal sinus of a patient, the guidewire having a lumen. The apparatus also includes an optic fiber, traversing the lumen, configured to illuminate the distal end, and a coil, wound around the optic fiber and located within the lumen at the distal end, configured to generate a signal in response to a magnetic field interacting with the coil. A processor is configured to receive the signal and to evaluate a location of the distal end in response to the signal.

12 Claims, 6 Drawing Sheets

(51) Int. Cl.
- *A61B 17/24* (2006.01)
- *A61B 34/20* (2016.01)
- *A61B 1/233* (2006.01)
- *A61M 25/09* (2006.01)
- *A61B 90/00* (2016.01)
- *A61B 90/14* (2016.01)
- *A61B 90/30* (2016.01)

(52) U.S. Cl.
CPC ............ *A61B 34/20* (2016.02); *A61M 25/09* (2013.01); *A61B 90/14* (2016.02); *A61B 2034/2051* (2016.02); *A61B 2034/2065* (2016.02); *A61B 2034/2072* (2016.02); *A61B 2090/306* (2016.02); *A61B 2090/365* (2016.02); *A61B 2090/3614* (2016.02); *A61M 2025/0915* (2013.01); *A61M 2025/09083* (2013.01); *A61M 2025/09108* (2013.01); *A61M 2025/09183* (2013.01)

(58) Field of Classification Search
CPC .... A61B 2034/2072; A61B 2034/2065; A61B 2034/2051; A61B 2090/3614; A61B 2090/365; A61B 2090/3983; A61M 25/09; A61M 2025/09108; A61M 2025/09083; A61M 2025/0915; A61M 2025/09183
See application file for complete search history.

(56) References Cited

U.S. PATENT DOCUMENTS

| | | |
|---|---|---|
| 6,151,404 A | 11/2000 | Pieper |
| 6,167,296 A | 12/2000 | Shahidi |
| 6,346,940 B1 | 2/2002 | Fukunaga |
| 7,072,501 B2 | 7/2006 | Wood |
| 7,167,180 B1 | 1/2007 | Shibolet |
| 7,720,521 B2 | 5/2010 | Chang et al. |
| 7,822,461 B2 | 10/2010 | Geiger |
| 8,123,722 B2 | 2/2012 | Chang et al. |
| 8,190,389 B2 | 5/2012 | Kim et al. |
| 8,239,003 B2 | 8/2012 | Akins |
| 8,320,711 B2 | 11/2012 | Altmann et al. |
| 8,702,626 B1 | 4/2014 | Kim et al. |
| 8,764,683 B2 | 7/2014 | Meller et al. |
| 9,155,492 B2 | 10/2015 | Jenkins et al. |
| 9,167,961 B2 | 10/2015 | Makower et al. |
| 9,198,736 B2 | 12/2015 | Kim et al. |
| 9,468,362 B2 | 10/2016 | Goldfarb et al. |
| 2006/0004286 A1* | 1/2006 | Chang ............. A61B 5/06 600/435 |
| 2007/0129751 A1 | 6/2007 | Muni |
| 2007/0208252 A1 | 9/2007 | Makower |
| 2008/0183073 A1 | 7/2008 | Higgins |
| 2008/0255446 A1 | 10/2008 | Akins |
| 2009/0297001 A1 | 12/2009 | Markowitz |
| 2010/0030031 A1 | 2/2010 | Goldfarb et al. |
| 2010/0241155 A1 | 9/2010 | Chang |
| 2011/0004057 A1 | 1/2011 | Goldfarb et al. |
| 2011/0060214 A1 | 3/2011 | Makower |
| 2012/0063644 A1 | 3/2012 | Popovic |
| 2012/0078118 A1 | 3/2012 | Jenkins et al. |
| 2012/0099778 A1 | 4/2012 | Helm |
| 2012/0172761 A1 | 7/2012 | Meller et al. |
| 2012/0245456 A1 | 9/2012 | Kim |
| 2012/0265094 A1 | 10/2012 | Goldfarb et al. |
| 2014/0121676 A1 | 5/2014 | Kostrzewski |
| 2014/0200444 A1 | 7/2014 | Kim et al. |
| 2014/0364725 A1 | 12/2014 | Makower |
| 2016/0004286 A1 | 1/2016 | Collopy et al. |
| 2016/0007842 A1 | 1/2016 | Govari et al. |
| 2016/0183841 A1 | 6/2016 | Duindam |

FOREIGN PATENT DOCUMENTS

| | | |
|---|---|---|
| EP | 1095628 | 5/2001 |
| JP | 2007-209531 | 6/2013 |
| WO | WO 2008/036050 | 3/2008 |
| WO | WO 2008/111070 | 9/2008 |
| WO | WO 2010/046802 | 4/2010 |
| WO | WO 2010/140074 | 12/2010 |
| WO | WO 2014/093880 | 6/2014 |

OTHER PUBLICATIONS

Yamashita, Juli, et al. "Real-time 3-D Model-Based Navigation System for Endoscopic Paranasal Sinus Surgery." IEEE Transactions on biomedical engineering 46.1 (1999): 107-116.
Australian Office Action dated Mar. 26, 2019 for Application No. 2015287957, 3 pages.
Australian Office Action dated Apr. 01, 2019 for Application No. 2015287961, 3 pages.
Chinese Office Action dated Mar. 15, 2018 for Application No. 201580037449.8, 14 pages.
Chinese Office Action dated Nov. 29, 2018 for Application No. 201580037449.8, 13 pages.
European Office Action dated Feb. 15, 2019 for Application No. 15747615.1, 7 pages.
International Search Report and Written Opinion dated Oct. 08, 2015 for Application No. PCT/US2015/039501, 12 pgs.
International Search Report and Written Opinion dated Oct. 12, 2015 for Application No. PCT/US2015/039506, 13 pgs.
Japanese Office Action dated Jun. 4, 2019 for Application No. JP2017-501024.
U.S. Appl. No. 62/022,607, filed Jul. 9, 2014.
U.S. Appl. No. 62/052,391, filed Sep. 18, 2014.
Japanese Office Action—Application No. 2017-501016 dated Apr. 21, 2020.

* cited by examiner

GUIDEWIRE NAVIGATION FOR SINUPLASTY

CROSS-REFERENCE TO RELATED APPLICATIONS

This application claims priority to U.S. Provisional Patent App. No. 62/022,607, Jul. 9, 2014, entitled "Guidewire Navigation for Sinuplasty," the disclosure of which is incorporated by reference herein.

This application also claims priority to U.S. Provisional Patent App. No. 62/052,391, filed Sep. 18, 2014, entitled "Guidewire Navigation for Sinuplasty," the disclosure of which is incorporated by reference herein.

JOINT RESEARCH STATEMENT

Subject matter disclosed in this application was developed and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement include Biosense Webster (Israel) Ltd. and Acclarent, Inc.

FIELD OF THE INVENTION

The present invention relates generally to equipment used in invasive surgery, and specifically to guidewires used in such surgery.

BACKGROUND OF THE INVENTION

Particularly in nasal sinus surgery, including sinuplasty, positioning of instruments during the surgery is critical due to the proximity of the sinuses to sensitive features such as the brain and the optic nerves. Various methods are known in the patent literature for facilitating positioning of such instruments, including positioning of guidewires.

For example, U.S. Patent Application 2012/0265094, to Goldfarb et al., whose disclosure is incorporated herein by reference, describes a method that is useable to facilitate transnasal insertion and positioning of a guidewire. The method involves direct viewing of the guidewire via an endoscope.

U.S. Patent Application 2012/0078118, to Jenkins et al., whose disclosure is incorporated herein by reference, describes an illuminating guidewire device. The disclosure states that the device may be employed to provide transillumination, and may facilitate visualization of target anatomy.

Documents incorporated by reference in the present patent application are to be considered an integral part of the application except that, to the extent that any terms are defined in these incorporated documents in a manner that conflicts with definitions made explicitly or implicitly in the present specification, only the definitions in the present specification should be considered.

SUMMARY OF THE INVENTION

An embodiment of the present invention provides apparatus, including, a guidewire having a distal end, configured to be inserted into proximity with a nasal sinus of a patient, the guidewire having a lumen;

an optic fiber, traversing the lumen, configured to illuminate the distal end;

a coil, wound around the optic fiber and located within the lumen at the distal end, configured to generate a signal in response to a magnetic field interacting with the coil; and a processor, configured to receive the signal and to evaluate a location of the distal end in response to the signal.

In a disclosed embodiment the apparatus may also include one or more magnetic field generators fixedly positioned in proximity to the nasal sinus, configured to generate the magnetic field. Typically the processor is configured to register a location of the one or more magnetic field generators with the patient.

In a further disclosed embodiment the apparatus also includes a core-wire, traversing the lumen, configured to stabilize the guidewire.

In a yet further disclosed embodiment the processor is configured to incorporate an indication of the location of the distal end into a displayed image of the patient. Typically, the processor is configured to recognize the nasal sinus in a received image of the patient, and to indicate the recognized nasal sinus in the displayed image.

There is further provided, according to an embodiment of the present invention embodiment of the present invention, a method, including, providing a guidewire having a distal end, the guidewire having a lumen;

inserting an optic fiber, configured to illuminate the distal end, to traverse the lumen;

winding a coil, configured to generate a signal in response to a magnetic field interacting with the coil, around the optic fiber;

locating the coil within the lumen at the distal end;

inserting the distal end of the guidewire into proximity with a nasal sinus of a patient; and receiving the signal and evaluating a location of the distal end in response to the received signal.

There is further provided, according to an embodiment of the present invention embodiment of the present invention, apparatus, including, a guidewire having a distal end, configured to be inserted into proximity with a nasal sinus of a patient, the guidewire having a lumen;

a core-wire, traversing the lumen, configured to stabilize the guidewire;

a coil, encircling the core-wire and located within the lumen at the distal end, configured to generate a signal in response to a magnetic field interacting with the coil; and a processor, configured to receive the signal and to evaluate a location of the distal end in response to the signal.

The present disclosure will be more fully understood from the following detailed description of the embodiments thereof, taken together with the drawings, in which:

DETAILED DESCRIPTION OF EMBODIMENTS

Overview

In a typical sinuplasty procedure, a guidewire is inserted into the nasal sinus of a patient until the distal tip of the guidewire is positioned beyond a site within the sinus where the procedure is to be performed. Once the distal tip has been so positioned, a deflated balloon is slid along the guidewire until it reaches the procedure site. The balloon is then inflated to perform the sinuplasty procedure, the balloon inflation typically causing elements at the site, which are contacted by the balloon, to separate.

Accurate positioning of the guidewire distal tip is extremely important, since the tip is typically in close proximity to critical features of the patient such as the brain, the eyes, and/or the optic nerves. Prior art sinuplasty systems track the distal tip by illuminating the tip, using an optic fiber in the guidewire, with visible light. A physician performing the procedure observes the light emitted from the patient's skin, and uses this observation to track the tip. However, the light originating at the distal tip and emitted from the skin has been dispersed and absorbed by elements such as blood, cartilage, and bone, so that the light visible to the physician does not allow the physician to accurately know the location of the tip.

An embodiment of the present invention overcomes this problem by providing an alternative tracking method for the physician. A guidewire, which is configured to be inserted into proximity with a nasal sinus of a patient, is formed with a lumen. An optic fiber that traverses the lumen is configured to illuminate the distal end of the guidewire. A coil is wound around the optic fiber, the coil being located within the lumen at the distal end of the guidewire. Winding the coil around the optic fiber ensures efficient use of space at the distal end of the guidewire. The coil generates a signal in response to a magnetic field interacting with the coil, and a processor receives the signal and evaluates the location of the distal end of the guidewire in response to the received signal.

The magnetic field used to interact with the coil may be generated from field generators that are placed in a frame clamped to the patient's head.

The processor typically uses the evaluated location to superimpose an indication of the location of the distal tip on an image of the patient, and the superposition allows the physician to accurately track the position of the guidewire.

System Description

Figure 1:
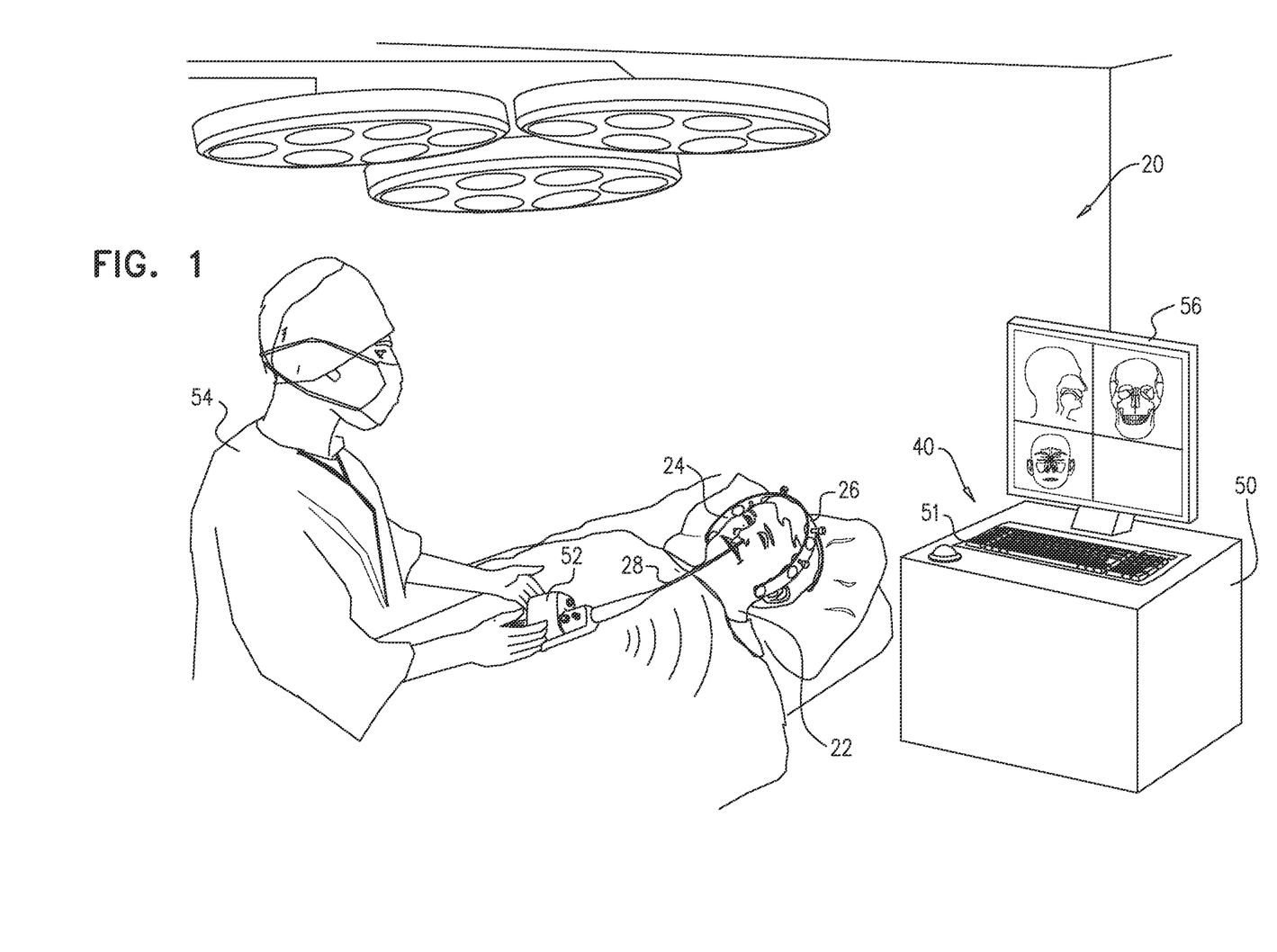
FIG. 1 is a schematic illustration of a sinus surgery system, according to an embodiment of the present invention.
Figure 2:
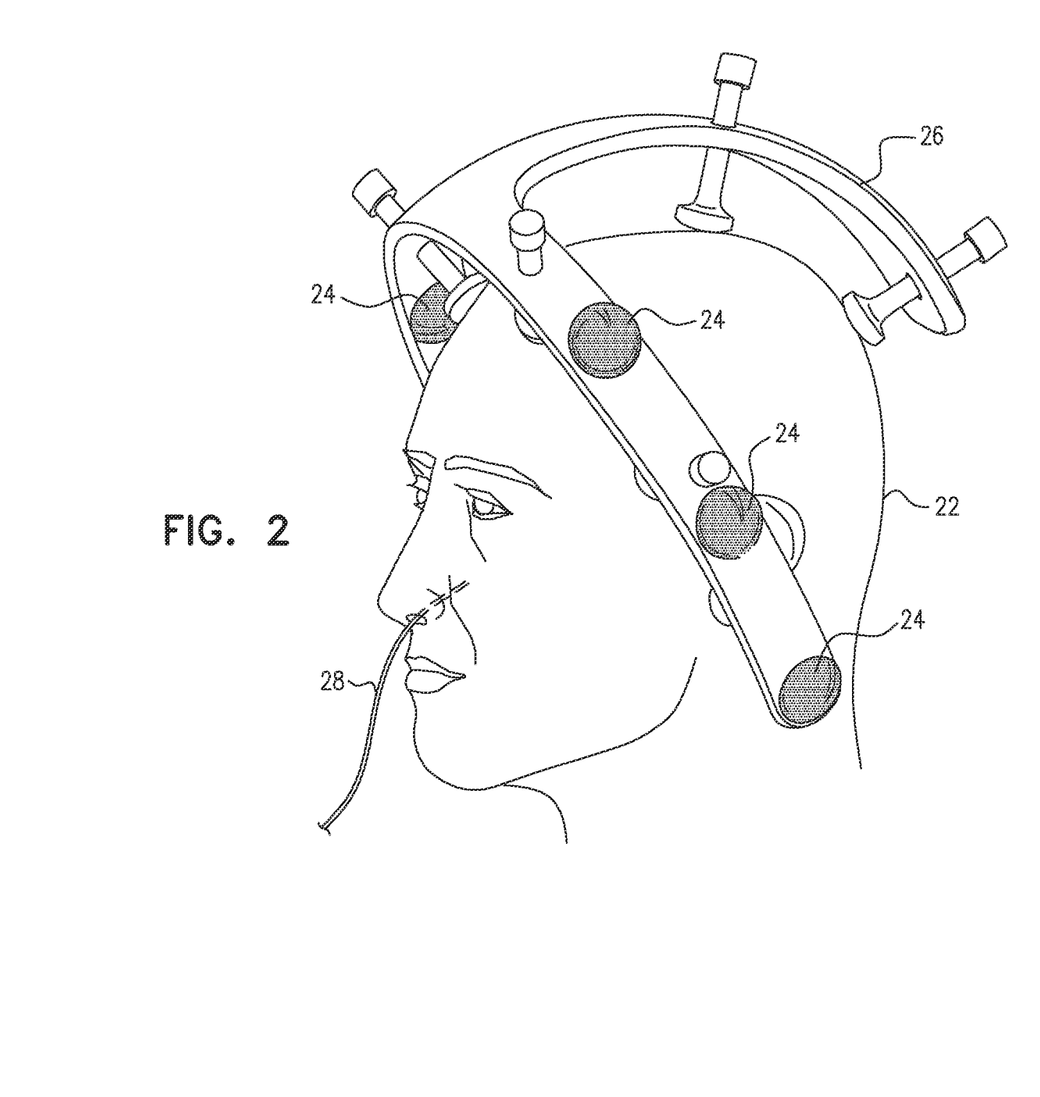
FIG. 2 is a schematic illustration of the head of a patient undergoing surgery with the system of FIG. 1, according to an embodiment of the present invention.

Reference is now made to FIG. 1, which is a schematic illustration of a sinus surgery system 20, and to FIG. 2, which is a schematic illustration of the head of a patient 22 undergoing surgery with the system, according to an embodiment of the present invention. System 20 is typically used during a sinuplasty procedure on a nasal sinus of patient 22. Prior to such a sinuplasty procedure, a set of magnetic field generators 24 are fixed to the head of the patient, typically by incorporating the generators into a frame 26 which is clamped to the patient's head. As is explained below, the field generators enable the position of a guidewire 28 that is inserted into the nasal sinus of the patient to be tracked.

Elements of system 20, including generators 24, may be controlled by a system processor 40, comprising a processing unit communicating with one or more memories. Processor 40 may be mounted in a console 50, which comprises operating controls 51 that typically include a keypad and/or a pointing device such as a mouse or trackball. Console 50 also connects to other elements of system 20, such as a proximal end 52 of catheter 24. A physician 54 uses the operating controls to interact with the processor while performing the procedure, and the processor may present results produced by system 20 on a screen 56.

Processor 40 uses software stored in a memory of the processor to operate system 20. The software may be downloaded to processor 40 in electronic form, over a network, for example, or it may, alternatively or additionally, be provided and/or stored on non-transitory tangible media, such as magnetic, optical, or electronic memory.

Processor 40 uses the software, inter alia, to operate and calibrate magnetic generators 24. The generators are operated so as to transmit alternating magnetic fields of different frequencies into a region in proximity to frame 26. Prior to being placed on the patient, the generators in the frame may be calibrated by positioning a coil in the region in known locations and orientations relative to the frame. Signals are induced in the coil by the alternating magnetic fields, and the processor acquires and records the signals. The processor then formulates a calibration relationship between the locations and orientations of the coil, and the recorded signals for these locations and orientations.

Once the calibration relationship has been formulated, the frame may be placed on the patient's head. After placement, the frame is fixed in position, and registered with external features of the patient's head, for example by imaging the patient's head with the attached frame from a number of different angles. The frame registration also registers the magnetic field generators with the patient's external features. Alternatively or additionally, the registration may include placing a coil in one or more known locations and orientations with respect to the external features of the patient as well as with the frame. The Carto® system produced by Biosense Webster, of Diamond Bar, Calif., uses a system similar to that described herein for finding the location and orientation of a coil in a region irradiated by magnetic fields.

In addition to registering with the patient's external features, the registration typically includes registration with an image of the patient's sinuses which has typically been acquired prior to a projected sinuplasty procedure. The image used may typically comprise a CT (computerized tomography), MRI (magnetic resonance imaging) or an ultrasound image, or a combination of such images. Thus frame 26 is in registration with the patient's sinuses and with the patient's external features.

Figure 3A:
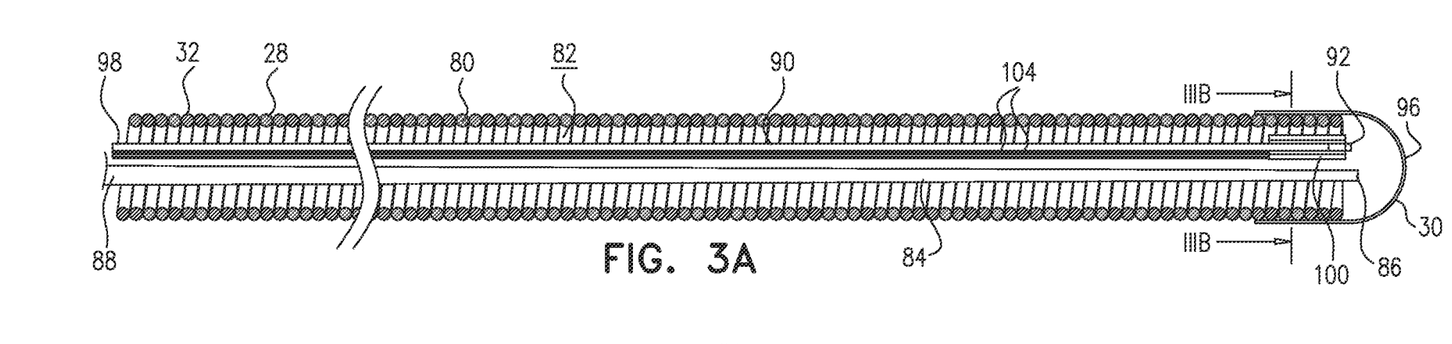
FIGS. 3A and 3B are schematic diagrams of a guidewire, according to an embodiment of the present invention.
Figure 3B:
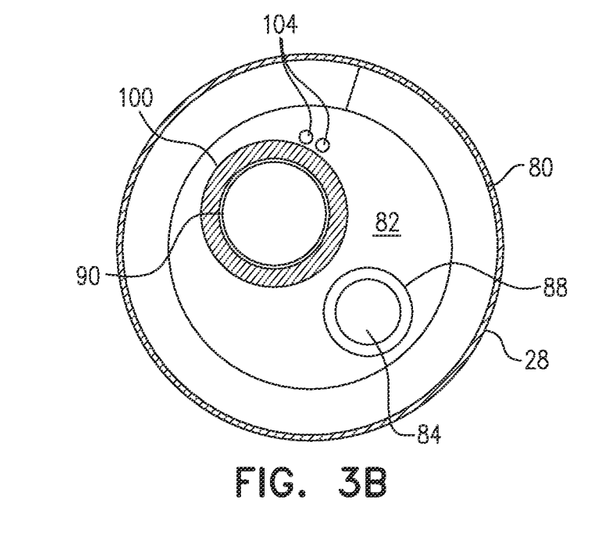

FIGS. 3A and 3B are schematic diagrams of guidewire 28, according to an embodiment of the present invention. FIG. 3A is a schematic longitudinal section of the guidewire, and FIG. 3B is a schematic cross-section, taken along a line IIIB-IIIB, of the guidewire. Guidewire 28 comprises an outer coil 80 having an internal lumen 82, and the coil is typically formed from non-ferromagnetic material, such as 316 stainless steel, titanium, cobalt-chrome, nitinol, and MP35N steel alloy, although the coil is not limited to these materials. In an embodiment, typical nominal external and internal diameters of the coil are 0.9 mm and 0.6 mm respectively. The guidewire has a distal end 30 and a proximal end 32.

A tapered nitinol core-wire 84 traverses the length of the lumen, the core-wire having a distal end 86 and a proximal end 88. The taper of the core-wire, at the distal end, is typically formed by centerless grinding. In a disclosed embodiment, a proximal diameter of the core-wire is in a range of 0.25 mm-0.35 mm and a distal diameter is between 0.01 mm and 0.015 mm. A typical length of the taper of the core-wire is 10 cm, while a typical length of the core-wire as a whole ranges between 40 cm and 80 cm. Core-wire 84 is typically used to stabilize the shape of the guidewire, by being attached in at least two locations, normally by soldering, to outer coil 80. The core-wire, when attached, provides flexural and torsional characteristics to the guidewire that, inter alia, prevent the guidewire from "winding up" when the user rotates the proximal end. The superelasticity of the nitinol allows the guidewire to undergo considerable bending while still being able to return to its unbent state.

In addition to core-wire 84, an optic fiber 90 is inserted into lumen 82 so as to traverse the length of the lumen. A distal end 92 of the optic fiber is configured to be in proximity to a transparent lens 96, which is connected to, and which acts as a termination for, outer coil 80. A lamp (not shown in the figure) is coupled to a proximal end 98 of the optic fiber, and is operated by processor 40 so as to illuminate lens 96 with visible light. Optic fiber 90 may comprise a single strand of fiber. Alternatively optic fiber 90 may comprise a two or more strands of optical fibers.

Optic fiber 90 is typically formed from plastic or glass. A plastic fiber typically has a lower transmissivity than a glass fiber, but may be less prone to breaking if the fiber is sharply bent. In one embodiment optic fiber 90 comprises two plastic strands each having a diameter of 250 microns. In alternative embodiments optic fiber 90 comprises a single glass strand having a diameter of 150 microns or 200 microns.

Prior to insertion of the optic fiber into lumen 82, a magnetic field sensing coil 100 is wound around distal end 92 of optic fiber 90, so that after insertion the sensing coil is positioned at distal end 30 of guidewire 28. The sensing coil thus has an internal diameter corresponding to the external diameter of optic fiber 90. In some embodiments there is a small gap, typically approximately 25 microns, between the internal circumference of the sensing coil and the external circumference of the optic fiber. In one embodiment coil 100 has an external diameter of 0.45 mm, although other embodiments may have coil external diameters larger or smaller than 0.45 mm. The two ends of coil 100 are typically connected by conducting wires 104 which traverse the length of lumen 82. The conducting wires are connected to circuitry, typically in console 50, which is configured to enable processor 40 to measure and record signal levels generated by the two ends of coil 100. Alternatively, the signal levels may be at least partially conveyed wirelessly to the circuitry.

Figure 4A:
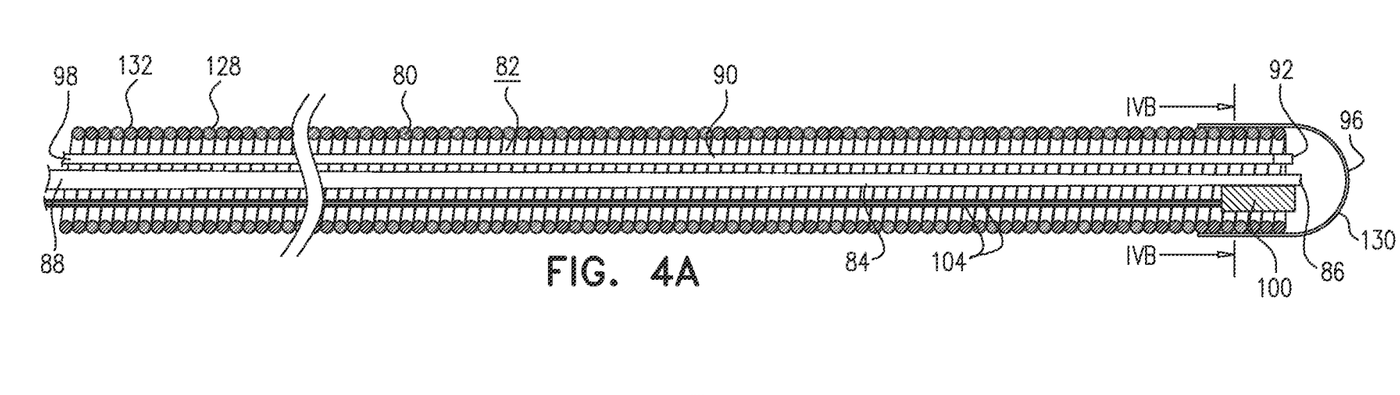
FIGS. 4A and 4B are schematic diagrams of a guidewire, according to an alternative embodiment of the present invention.
Figure 4B:
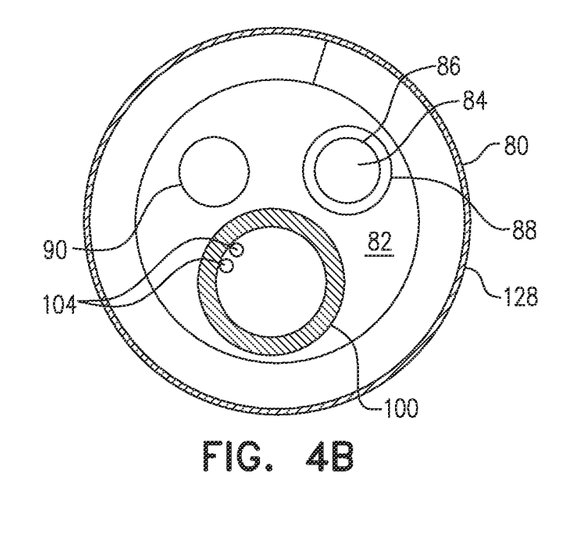

FIGS. 4A and 4B are schematic diagrams of a guidewire 128, according to an alternative embodiment of the present invention. FIG. 4A is a schematic longitudinal section of guidewire 128, and FIG. 4B is a schematic cross-section, taken along a line IVB-IVB, of the guidewire. Guidewire 128 has a distal end 130 and a proximal end 132. Apart from the differences described below, the operation of guidewire 128 is generally similar to that of guidewire 28 (FIGS. 3A and 3B), and elements indicated by the same reference numerals in both guidewires 28 and 128 are generally similar in construction and in operation. Thus, guidewire 128 may be used in place of guidewire 28 in system 20.

In contrast to guidewire 28, coil 100 in guidewire 128 is not wound around optic fiber 90. Rather, coil 100, while being positioned within lumen 82 at the distal end of guidewire 128, i.e. at distal end 130, is separate from both core-wire 84 and optic fiber 90. Signal levels from the coil are transferred to circuitry, described above with reference to FIGS. 3A, 3B, enabling processor 40 to measure and record the signal levels. As is also described above, the transfer may be via wires 104 or wirelessly.

Guidewire 128 also comprises tapered, core-wire 84, extending the length of lumen 82. As for guidewire 28, core-wire 84 acts to stabilize guidewire 128.

Figure 5A:
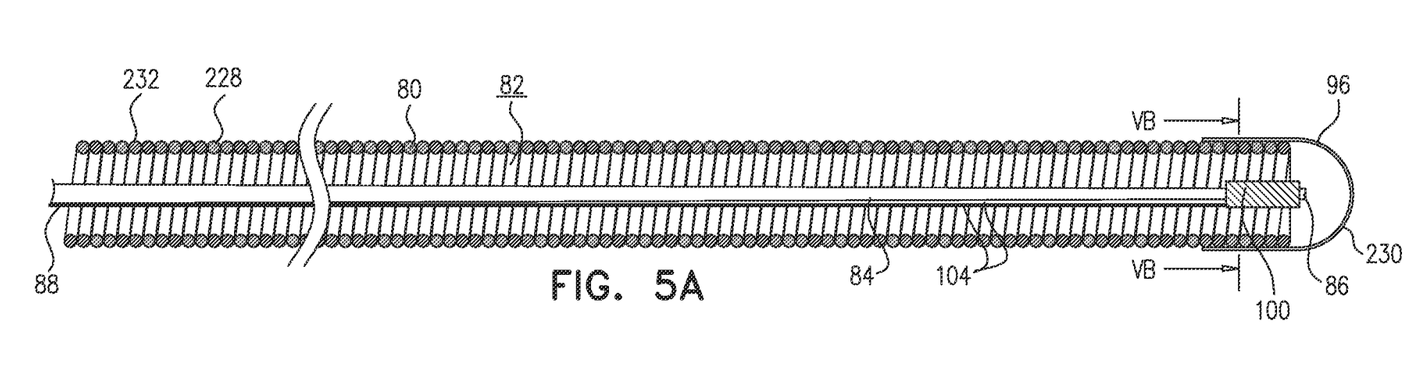
FIGS. 5A and 5B are schematic diagrams of a guidewire, according to a further alternative embodiment of the present invention.
Figure 5B:
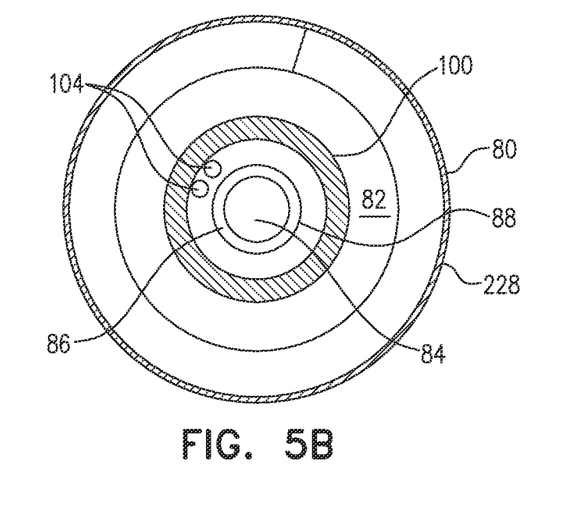

FIGS. 5A and 5B are schematic diagrams of a guidewire 228, according to a further alternative embodiment of the present invention. FIG. 5A is a schematic longitudinal section of guidewire 228, and FIG. 5B is a schematic cross-section, taken along a line VB-VB, of the guidewire. Guidewire 228 has a distal end 230 and a proximal end 232. Apart from the differences described below, the operation of guidewire 228 is generally similar to that of guidewire 28 (FIGS. 3A and 3B), and elements indicated by the same reference numerals in both guidewires 28 and 228 are generally similar in construction and in operation. Thus, guidewire 228 may be used in place of guidewire 28 in system 20.

In guidewire 228 coil 100 is configured to encircle distal end 86 of core-wire 84. Typically, an inside diameter of coil 100 is larger than an external diameter of core-wire 84, and the coil may be fixed by any convenient means, such as epoxy cement, (not shown in the figure) to the core-wire. Signal levels generated by the coil are transferred to processor 40, substantially as described above for guidewires 28 and 128. In some embodiments of guidewire 228 there is an optic fiber, similar in functionality and characteristics to optic fiber 90, located in and traversing the length of lumen 82. Alternatively, as illustrated in the figure, there is no optic fiber in guidewire 228.

In a sinuplasty procedure, a guidewire such as guidewire 28, 128, or 228, is inserted into a nasal sinus. The circuitry coupled to coil 100 acquires signals from the coil, while generators 24 are transmitting their magnetic fields. The processor applies the calibration relationship referred to above to the signals, and together with the registration also described above finds the location and orientation of the coil. An indication of the location and orientation of the coil, i.e., of the distal tip of the guidewire, may be overlaid onto a registered image of the patient's sinuses, the image having typically been acquired prior to the procedure. The image used may typically comprise a CT (computerized tomography), MRI (magnetic resonance imaging) or an ultrasound (US) image, or a combination of such images. The composite image, of the sinuses and the guidewire distal tip, may be displayed to physician 54 on screen 56 (FIG. 1). A more detailed description of such a use of a guidewire in real-time surgery is provided with respect to the flowchart of FIG. 6, below.

Figure 6:
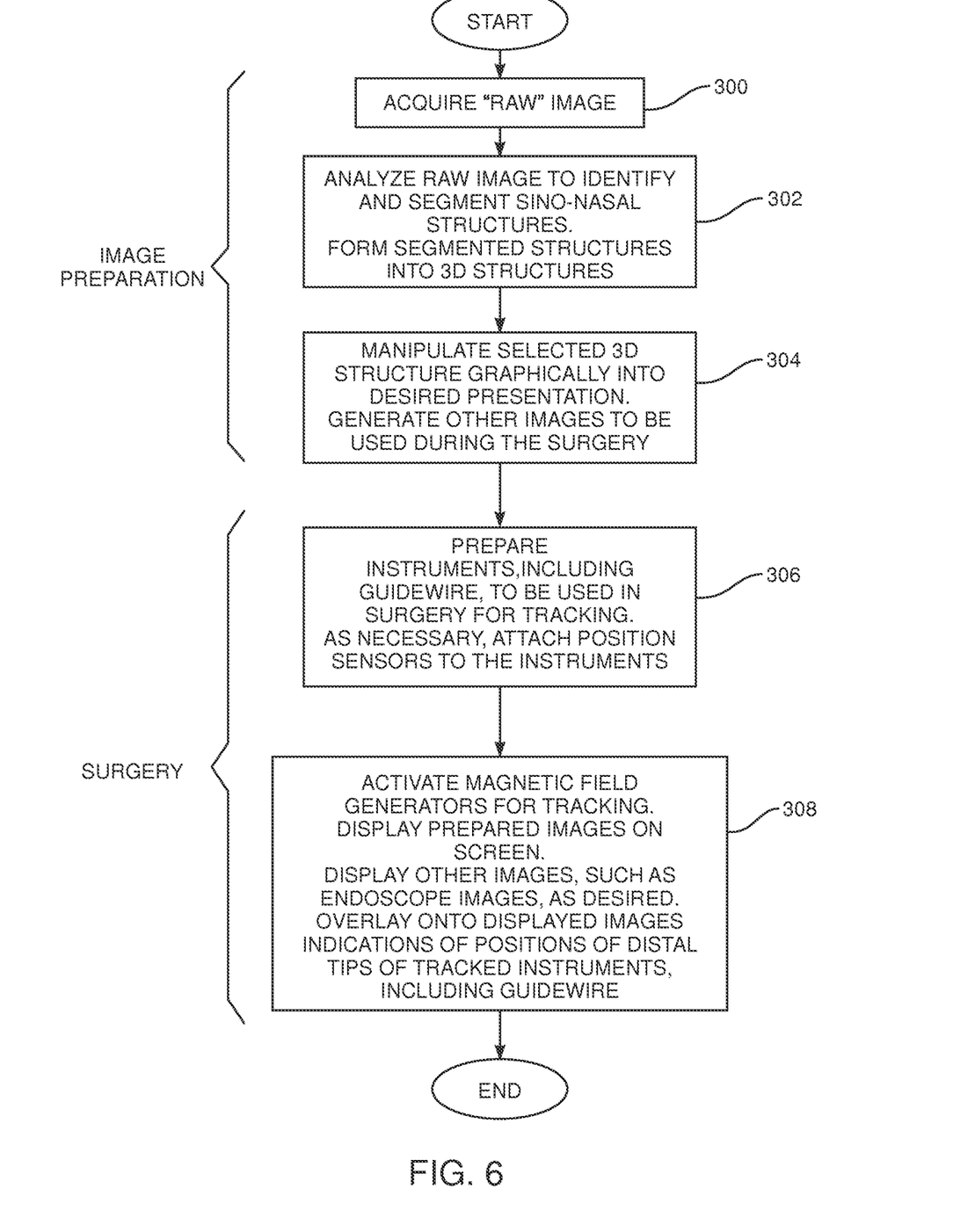
FIG. 6 is a flowchart of steps taken for performance of nasal sinus surgery, according to an embodiment of the present invention.

FIG. 6 is a flowchart of steps taken for performance of nasal sinus surgery, according to an embodiment of the present invention. The surgery is assumed by way of example to be performed on the ostium and outflow tract of a peripheral sinus, but those having ordinary skill in the art will be able to adapt the description, mutatis mutandis, for other types of sinus surgery.

The steps of the flowchart assume that the distal tip of a guidewire such as one of those described hereinabove is tracked in real-time during the course of the surgery, by the magnetic tracking system described above. For clarity, in the flowchart description hereinbelow guidewire 28 is assumed to be used, and those having ordinary skill in the art will be able to modify the description for the use of other guidewires, such as guidewire 128 or guidewire 228.

The distal tips of other instruments used during the surgery, such as the distal tip of an endoscope, may also be tracked by the magnetic tracking system by incorporating respective coils into the instrument distal tips for flexible or rigid instruments, as is known in the art. Such instruments, which may typically be used for rhinological surgery, including Functional Endoscopic Sinus Surgery (FESS) and balloon-assisted FESS, i.e., balloon sinuplasty, are commercially available.

For rigid instruments, the tracking coil may alternatively be positioned in a proximal portion of the instrument, provided that the magnetic tracking system has been programmed to make the spatial adjustments required to convert the signals received from the coil. Such a method for tracking is also known in the art.

In a preparatory step 300 a "raw" image of the anatomy to be operated on is acquired. The raw image may comprise a CT image, an MRI image, or a US image, of the cranium. In some embodiments more than one such image is combined and the composite image produced, after registration of the combined images, is used as the raw image. Images are typically in a Digital Imaging and Communications in Medicine (DICOM) format.

In a first analysis step 302, the raw image is analyzed to isolate sino-nasal structures in the image. The analysis applies recognition algorithms to point clouds derived from the images so as to generate the different structures. The algorithms are used to segment the image, and to form the segmented sections into three-dimensional (3D) structures.

The algorithms used may be based on "seeded region growing" algorithms such as those described in the paper "Comparison of 3D Segmentation Algorithms for Medical Imaging," by Hakan et al., published in the Twentieth IEEE International Symposium on Computer-Based Medical Systems, 2007, CBMS '07, which is incorporated herein by reference. Alternatively or additionally, the recognition referred to herein may be implemented using commercially available software, such as the OsiriX 6.5 image processing software produced by Pixmeo of Bernex, Geneva, Switzerland, or the Mimics software produced by Materialise Inc. of Leuven, Belgium.

The points within the 3D structures generated have coordinates which enable any given structure to be transformed. For example, a given structure may be translated or rotated, or other types of transformation may be applied to the structure.

In an image manipulation step 304, the 3D structures generated in step 302 are presented to physician 54 on a screen, herein assumed by way of example to be screen 56. The physician uses operating controls 51 to manipulate the image so that the region to be operated on is clearly visible. To this end the physician may rotate, pan, and/or zoom the image, and/or generate one or more cross-sections of the image. In addition, the physician may vary the transparency and/or color of the different structures. The manipulation typically includes highlighting of a region that includes the region to be operated on. For the outflow tracts considered here, such highlighting may conveniently be achieved by applying a sinus outflow tract recognition algorithm to the manipulated image. The recognition may use an algorithm similar to that referred to above in step 302, and/or may be implemented using the commercial software also referred to above.

Other images that may be generated in step 304 include displays of planned surgical steps, paths to be taken by instruments, and structures in proximity to the outflow tracts.

Step 304 concludes an image preparation phase that is implemented prior to performance of the nasal sinus surgery. The following steps of the flowchart describe actions that may be taken during the surgery.

In an instrument preparation step 306, instruments to be used in the surgery are prepared so that they can be tracked during the surgery. The instruments include guidewire 28, as described hereinabove, which can be tracked by system 20 using sensing coil 100.

The instruments typically also include an endoscope, and may also include one or more flexible instruments and one or more catheters. The instruments may further include, but are not limited to, one or more of the following: Grasping forceps, cutting forceps, including Blakesly forceps and Blakesly throughcutting forceps, irrigation cannulae, suction cannulae, including Frazier and Yankauer suction cannulae, balltipped probe, sinus seeker, Freer elevator, Coddle elevator, other elevators, J-curettes or other curettes, punches, including mushroom punches, injection needles, needle drivers, monopolar or bipolar electrocautery probes, RF ablation probes, laser-energy transmitting probes, powered or manual microdebriders, shavers, drills, or burrs.

Any instruments that are to be used may have positional sensors, herein assumed to comprise electromagnetic positional sensors, attached to the instruments. Such sensors typically comprise coils similar to coil 100, and may be configured to be tracked by system 20, using magnetic fields from generators 24 to induce tracking signals in the coils. Alternatively, the sensors may be configured to use the Hall effect to generate the tracking signals. In the case of rigid instruments, the sensors may be mounted on a proximal portion of the instrument in a known fixed spatial relation with the instrument distal portion. If the instrument is flexible, the sensor is mounted on the distal portion of the instrument.

In some cases, a sensor may be built into an instrument at the time of manufacture. In other instances, it may be desirable to attach one or more sensors to an instrument prior to use of that instrument in surgery. A method for performing such attachment is described in U.S. Pat. No. 8,190,389 and U.S. Patent Publication 2012/0245456, both entitled "Adapter for Attaching Electromagnetic Image Guidance Components to a Medical Device," which are incorporated herein by reference.

In a final real-time procedure step 308 physician 54 activates generators 24 to begin the instrument tracking process. The physician also displays one or more images, typically multiple image panels, on screen 56. The images displayed typically include the real-time image formed by an endoscope used in the procedure, as well as the images prepared and generated in step 304.

An indication of the location and orientation of the endoscope distal end may be overlaid, in registration, on the outflow tracts image generated in step 304. Similarly, an indication of the location and orientation of the distal tip of guidewire 28 may also be overlaid, in registration, with the outflow tracts image.

As other instruments are introduced into the patient, their location and orientation may also be overlaid on the outflow tracts image.

The endoscope image referred to above may have superimposed upon it the image of the outflow tracts generated in image manipulation step 304, as well as one or more images of other structures that may have been generated in the image manipulation step.

Typically, the images displayed on screen 56 may be manipulated by the physician so as to improve the visibility of desired portions of the image, and so as to reduce "noise" in the presented image. Such manipulation typically includes the physician being able to render sections of the image, typically "outer" sections, to be at least partially transparent, so that inner sections of the image, including the indications of the distal tips of instruments used, including guidewire 28, are more visible. Alternatively or additionally, the manipulation may include the physician applying "false" color to sections of the image representing specific anatomical structures that have been segmented in step 302.

Because the location and orientation of the distal tip of guidewire 28 are known in real-time, cross-sections or slices of the anatomy in proximity to the distal end of the guidewire may be generated and displayed on screen 56 by system 20. For example, a cross-section of the anatomy ahead of the guidewire distal tip may be displayed.

Other images that may be presented on screen 56 include displays of planned surgical steps, paths to be taken by instruments, and structures in proximity to the structure being operated on. As stated above, such images are typically generated in image manipulation step 304.

While the images on screen 56, including the different image panels may be actuated and/or adjusted using controls 51, in some embodiments physician 54 uses voice activation, or another non-tactile method of activation, for such actuation or adjustment.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. Apparatus, comprising,
    a guidewire having a distal end, configured to be inserted into proximity with a nasal sinus of a patient, the guidewire having a lumen;
    an optic fiber, traversing the lumen, configured to illuminate the distal end;
    a sensing coil, wound around the optic fiber and located within the lumen at the distal end, configured to generate a signal in response to a magnetic field interacting with the sensing coil; and
    a processor, configured to receive the signal and to evaluate a location of the distal end in response to the signal, wherein the sensing coil has an internal diameter corresponding to the external diameter of the optic fiber and further comprising a gap of approximately 25 microns between the internal circumference of the sensing coil and the external circumference of the optic fiber.

2. The apparatus according to claim 1, and comprising one or more magnetic field generators fixedly positioned in proximity to the nasal sinus, configured to generate the magnetic field.

3. The apparatus according to claim 2, wherein the processor is configured to register a location of the one or more magnetic field generators with the patient.

4. The apparatus according to claim 1, and comprising a core-wire, traversing the lumen, configured to stabilize the guidewire.

5. The apparatus according to claim 1, wherein the processor is configured to incorporate an indication of the location of the distal end into a displayed image of the patient.

6. The apparatus according to claim 5, wherein the processor is configured to recognize the nasal sinus in a received image of the patient, and to indicate the recognized nasal sinus in the displayed image.

7. A method, comprising,
    providing a guidewire having a distal end, the guidewire having a lumen;
    inserting an optic fiber, configured to illuminate the distal end, to traverse the lumen;
    winding a sensing coil, configured to generate a signal in response to a magnetic field interacting with the sensing coil, around the optic fiber;
    locating the sensing coil within the lumen at the distal end;
    inserting the distal end of the guidewire into proximity with a nasal sinus of a patient; and
    receiving the signal and evaluating a location of the distal end in response to the received signal, wherein the sensing coil has an internal diameter corresponding to the external diameter of the optic fiber and further comprising a gap of approximately 25 microns between the internal circumference of the sensing coil and the external circumference of the optic fiber.

8. The method according to claim 7, and comprising fixedly positioning one or more magnetic field generators, configured to generate the magnetic field, in proximity to the nasal sinus.

9. The method according to claim 8, and comprising registering a location of the one or more magnetic field generators with the patient.

10. The method according to claim 7, and comprising inserting a core-wire to traverse the lumen, the core-wire being configured to stabilize the guidewire.

11. The method according to claim 7, and comprising incorporating an indication of the location of the distal end into a displayed image of the patient.

12. The method according to claim 11, and comprising recognizing, by a processor, the nasal sinus in a received image of the patient, and indicating the recognized nasal sinus in the displayed image.

* * * * *